(12) United States Patent
Chase (10) Patent No.: US 11,998,307 B2
(45) Date of Patent: Jun. 4, 2024

(54) CONTINUOUS BLOOD GLUCOSE MONITOR

(71) Applicant: Arnold Chase, West Hartford, CT (US)

(72) Inventor: Arnold Chase, West Hartford, CT (US)

( * ) Notice: Subject to any disclaimer, the term of this patent is extended or adjusted under 35 U.S.C. 154(b) by 1070 days.

(21) Appl. No.: 16/864,778

(22) Filed: May 1, 2020

(65) Prior Publication Data

US 2020/0253502 A1 Aug. 13, 2020

Related U.S. Application Data

(60) Continuation-in-part of application No. 16/856,100, filed on Apr. 23, 2020, which is a division of
(Continued)

(51) Int. Cl.
*A61B 5/0507* (2021.01)
*A61B 5/00* (2006.01)
(Continued)

(52) U.S. Cl.
CPC .......... *A61B 5/0507* (2013.01); *A61B 5/0004* (2013.01); *A61B 5/14532* (2013.01);
(Continued)

(58) Field of Classification Search
CPC . A61B 5/0507; A61B 5/0004; A61B 5/14532; A61B 5/1495; A61B 5/6824;
(Continued)

(56) References Cited

U.S. PATENT DOCUMENTS

| 7,613,488 B1 | 11/2009 | Maracas et al. |
| 2008/0200790 A1 | 8/2008 | Kim et al. |

(Continued)

FOREIGN PATENT DOCUMENTS

| CN | 205126252 U | 4/2016 |
| EP | 2 425 770 A1 | 3/2012 |

(Continued)

OTHER PUBLICATIONS

Chinese Office Action and its English translation dated Oct. 7, 2023 of corresponding Chinese Application No. 20180092336.1.
(Continued)

*Primary Examiner* — Christian Jang
(74) *Attorney, Agent, or Firm* — McCormick, Paulding & Huber PLLC (57) ABSTRACT

A continuous blood glucose monitoring system and method measures emitted microwave energy transmitted to and accepted by blood vessels in a desired target area of a patient in order to determine, in real time and in vivo, appropriate blood glucose levels. A measurement unit comprises a transmitter operatively connected to an antenna to deliver energy towards appropriate subcutaneous blood vessels. The measurement unit determines an accepted energy power value in the blood vessels associated with the desired target area. This measurement energy power value is compared with a calibration value, and the difference is used to determine a resultant blood glucose value. The determined blood glucose value may further be acclimatized using additional sensed values compensating for biological and ambient factors relevant to the patient. The final determined blood glucose value can be displayed for reading and/or transmitted and stored for recording for further reference.

12 Claims, 5 Drawing Sheets

Related U.S. Application Data application No. 16/118,827, filed on Aug. 31, 2018, now Pat. No. 10,631,753.

(60) Provisional application No. 62/646,510, filed on Mar. 22, 2018.

(51) Int. Cl.
  *A61B 5/145* (2006.01)
  *A61B 5/1495* (2006.01)

(52) U.S. Cl.
  CPC .......... *A61B 5/1495* (2013.01); *A61B 5/6824* (2013.01); *A61B 5/7246* (2013.01); *A61B 5/742* (2013.01); *A61B 2562/0228* (2013.01)

(58) Field of Classification Search
  CPC ................. A61B 5/7246; A61B 5/742; A61B 2562/0228; A61B 5/4875
  See application file for complete search history.

(56) References Cited

U.S. PATENT DOCUMENTS

| | | |
|---|---|---|
| 2008/0319285 A1 | 12/2008 | Hancock |
| 2008/0319434 A1 | 12/2008 | Rick et al. |
| 2010/0114086 A1 | 5/2010 | Deem et al. |
| 2014/0273821 A1 | 9/2014 | Miller et al. |
| 2016/0192867 A1 | 7/2016 | Esenaliev |
| 2016/0317060 A1 | 11/2016 | Connor |
| 2016/0317070 A1 | 11/2016 | Sivaraman et al. |
| 2017/0156645 A1 | 6/2017 | Lin et al. |
| 2018/0020948 A1* | 1/2018 | Butterworth ......... A61B 5/0507 600/430 |
| 2018/0325431 A1* | 11/2018 | Guarin ................. A61B 5/0507 |

FOREIGN PATENT DOCUMENTS

| | | |
|---|---|---|
| GB | 2428093 A | 1/2007 |
| JP | 2009500096 A | 1/2009 |
| JP | 2010524589 A | 7/2010 |
| JP | 2010169396 A | 8/2010 |
| JP | 2017536147 A | 12/2017 |
| KR | 20090084409 A | 8/2009 |
| KR | 20150095602 A | 8/2015 |
| KR | 20170058187 A | 5/2017 |
| WO | 2007003955 A1 | 1/2007 |
| WO | 2016080911 A1 | 5/2016 |
| WO | 2017141024 A2 | 8/2017 |

OTHER PUBLICATIONS

Japanese Office Action for corresponding JP Application No. 2020-551393 dated Aug. 31, 2021.
Korean Office Action and its English translation for corresponding KR Application No. 10-2020-7030210 dated Nov. 26, 2021.
Japanese Decision of Refusal and its English translation for corresponding JP Application No. 2020-551393 dated May 17, 2022.
European Search Report for corresponding EP Application No. 18910356 dated Nov. 9, 2021.

* cited by examiner

CONTINUOUS BLOOD GLUCOSE MONITOR

CROSS-REFERENCE TO RELATED APPLICATIONS

This application is a continuation-in-part of U.S. patent application Ser. No. 16/856,100, filed Apr. 23, 2020, which is a divisional of U.S. patent application Ser. No. 16/118,827, filed Aug. 31, 2018, which claims the benefit of U.S. Provisional Patent Application No. 62/646,510, filed Mar. 22, 2018, each of which is incorporated herein by reference in its entirety.

TECHNICAL FIELD

The present disclosure generally relates to non-invasive, in vivo blood glucose measurement systems, and more particularly to a personalized subcutaneous blood glucose measurement and tracking system for instantaneous real-time readings of blood glucose values.

BACKGROUND

For decades, attempts have been made to develop a system for "real-time" direct reading, non-invasive measurement of glucose levels in the bloodstream. To date, these efforts have been unsuccessful primarily due to the inherent nature of glucose itself, which readily dissolves in blood, as well as the containment of the bloodstream in the human body, making a direct, non-invasive measurement of glucose residing in the bloodstream extremely difficult.

Historically, optical methods have been favored in attempts to measure blood glucose levels utilizing visible light, infra-red light, or by attempting to detect polarization changes caused by varying glucose levels in the blood. These efforts have repeatedly proven fruitless, as were other attempts at direct, non-invasive measurement of blood glucose levels.

Presently available continuous blood glucose monitoring systems, in reality, actually measure interstitial fluid glucose levels rather than directly measuring blood glucose levels. As a result, such "blood glucose" systems or meters do not provide "real time" blood glucose readings. In addition, such systems inherently suffer from a substantial time lag—generally about 20 minutes with the correlation of interstitial fluid measurements relative to blood glucose readings.

Although generally recognized that blood glucose levels have been able to be measured fairly accurately via microwave means in vitro under controlled laboratory conditions, prior art measuring equipment has lacked the ability to make these measurements in vivo. While clinically useful measurements may be possible in such fixed laboratory conditions, a mechanism and embodiment that allows for actual non-invasive blood glucose readings "in the field" has heretofore not existed, to say nothing about the automatic calibration mechanisms that are needed to develop these simple laboratory measuring devices into a system that is suitable for everyday use with actual living beings who exhibit individual physical variations and characteristics from one another.

In recent years systems designed to measure glucose levels in individuals have been developed. These systems are invasive in nature, and actually only approximate real-time blood glucose levels by measuring the glucose level of interstitial fluid in a person. Many of these systems label themselves as "continuous" glucose monitors, but in actuality they do not actually measure true blood glucose levels, nor are they truly continuous. In almost all cases, the monitors only take readings periodically, at most, once every five minutes, and the interstitial fluid that they measure does not match and is delayed from the true instant venous readings for a period of time, typically 10-20 minutes. Recent efforts have been made to incorporate and use various interstitial fluid algorithms to better estimate true venous readings, but the offered readings are still only estimates and not true blood glucose readings.

In a hospital or clinical setting, for instance, such as during an operation on diabetic patients, venous blood is frequently drawn and rushed to an on-site laboratory for testing in order to determine a true blood glucose level for said patient(s) in a timely fashion.

In view of the foregoing, there is a need for an actual (direct reading) blood glucose measurement system that is non-invasive and can be used in vivo without exhibiting the inherent measurement variation and time lag to determine blood glucose measurements generally associated with prior art "blood glucose" meters that are actually "interstitial fluid" measuring devices. Accordingly, it is a general object of the present invention to provide a novel blood glucose tracking system that provides a new, optimized and efficient approach to blood glucose measurement, tracking and monitoring, that is non-invasive, directly measuring blood glucose, and can be done in vivo without any measurement variation and time lag.

SUMMARY

The present invention, directed to a blood glucose tracking system and method, works differently than prior art "blood glucose" meters and prior attempts at non-invasive measurement devices. Instead of trying to duplicate the specialized and optimized equipment needed to measure the glucose level of a solution in a controlled laboratory setting, the present invention achieves an accurate determination of said glucose level directly from the bloodstream by measuring how much overall emitted microwave energy is transmitted to and subsequently accepted by blood vessels within a defined and fixed target area, and then comparing this instantaneous measurement value against a prior known calibration value. The difference between the instantaneous power reading measurement and the prior calibration power reading measurement is analyzed and calculated to determine a resultant blood glucose value, which may further be acclimatized through additional sensed values that compensate for varying biological or ambient factors or changes relative to the individual patient. Still further, the determined blood glucose value can be displayed for reading and/or transmitted and stored for recording for future reference.

Unlike all presently available continuous "blood-glucose" meters (which, as noted above, actually measure interstitial fluid rather than blood glucose directly), the blood glucose tracking system in accordance with the present invention actually reads the instantaneous glucose concentration in a bloodstream. Additionally, unlike prior art meters that read interstitial fluid, the system reads and provides a blood-glucose value in real time without any time lag between measurement and actual blood-glucose readings. Still further, such real time measurements allow the blood glucose levels to be measured and monitored in vivo utilizing a compact measurement unit that can preferably be worn by the individual for in vivo use.

The system and method of the present invention is inherently different to other prior art systems and methods mainly in that the present invention relates to a direct absorptive measuring system, and uniquely does not depend on measuring transmitted energy that has been transmitted from a transmitting element through layers of skin and/or other body parts to a receiving element.

In accordance with preferred embodiments of the present invention, the system and method of blood glucose measurement utilizes a short duty-cycle, high impulse power/very-low average-power microwave energy transmitter. Blood composition averages about 92% water overall. It is a known fact that water-containing glucose absorbs microwave energy to an extent greater than water without glucose. By exploiting this phenomenon, there exists a practical pathway to finally being able to non-invasively detect and measure the instantaneous in-vivo level of glucose in the bloodstream. In accordance with preferred embodiments, the microwave energy from the energy source is fed into an antenna assembly designed to focus and transmit this energy toward appropriate subcutaneous blood vessels, namely, those blood vessels that are closest to the surface of the skin. In further preferred embodiments, the energy source and antenna assembly are provided in a housing mountable to the patient's body proximate subcutaneous blood vessels to be measured in a desired target area, more preferably mountable to the patient's arm, and even more preferably mountable to the patient's wrist, for example, as part of a placeable sensor.

A unique and important part of the system and method of blood glucose measurement in accordance with the present invention is the use of an individually tailored Radio Frequency (RF) mask that is created and customized for each target patient and that individual's optimal target area. Such an RF mask permits the transmitted microwave energy to only reach an exactly outlined target area of interest, such as, specific segments of near-surface blood vessels. Moreover, the microwave energy may be further contained, shaped and exclusively directed to a location and depth confirming to a specifically defined area that contains said "near surface" blood vessels by optimizing the antenna radiation lobe pattern(s), transmitted frequencies chosen, and power levels used, and individualized RF mask pattern. The same RF mask that limits the area(s) to which RF energy is directed and allowed to be transmitted also inherently limits the measurements of energy that otherwise would be absorbed outside of the desired target area, thus greatly increasing the accuracy of readings using the system and method of the present invention.

In an aspect of the present invention, the microwave energy is contained, shaped, and exclusively allowed to be directed towards a desired target area to a depth in a confirming specific area that contains subcutaneous blood vessels. The antenna assembly is preferably located adjacent to the RF mask which is placed over the desired target area. The design of the RF mask, which is larger than the footprint of the antenna assembly, allows for a physical X/Y axis adjustment or "slippage" of the antenna assembly without changing the amount of RF energy that is delivered to the target area, thus keeping the absorption amounts constant regardless of the exact location of the RF antenna over the RF mask. In embodiments, the antenna radiation lobe patterns, transmitted frequencies, and power levels can be varied with respect to specific patients and target areas on said patients.

In preferred embodiments of the present invention, the power levels needed to reach the targeted subcutaneous blood vessels are achieved by using low duty cycle, pulsed-type radio wave emissions, similar to those used by radar transmitters, and similarly the peak power levels may be adjusted as needed to optimize the readings of each individual.

In accordance with embodiments of the present invention, with each calibration, a known glucose value and its corresponding delivered power value could be placed into a memory buffer. As the test subject's glucose level changes, this would result in the average power level accepted by the bloodstream through the system to either rise or fall in value relative to a power value associated with the last calibration value. With each subsequent periodic microwave emission, the measurement unit would record all new data, and calculate blood glucose values based on an extrapolation of the change in the delivered/accepted power level between the instantaneous power level and previous calibration values.

Objects, features and advantages of the present invention will become apparent in light of the description of embodiments and features thereof, as enhanced by the accompanying figures.

BRIEF DESCRIPTION OF THE DRAWINGS

FIG. 6 illustrates a mask used on a patient to limit the area(s) to which energy transmitted from a measurement device in accordance with the present invention is allowed to be transmitted to.

DETAILED DESCRIPTION

Figure 1:
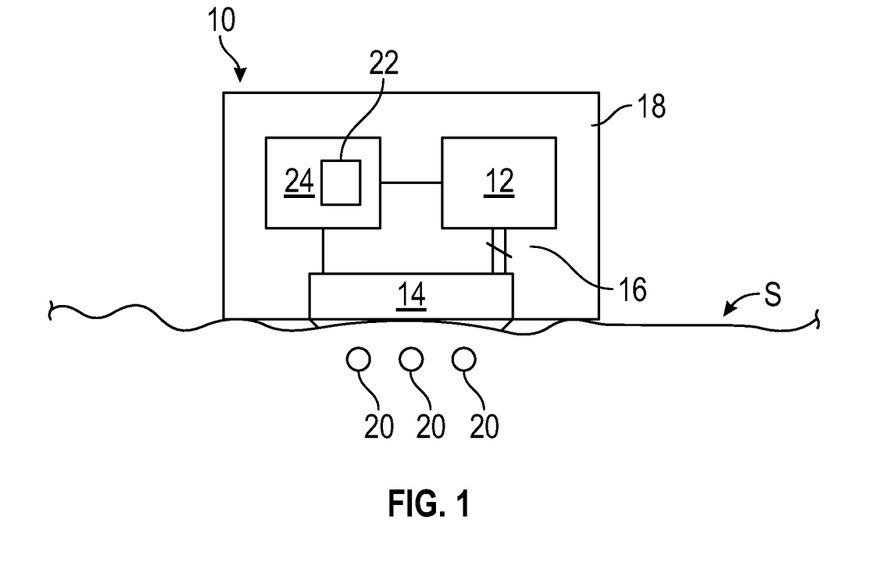
FIG. 1 illustrates a schematic embodiment of a blood glucose tracking system in accordance with the present invention for non-invasive in vivo blood glucose measurement.

Referring to FIG. 1, a schematic embodiment of a blood glucose tracking system for non-invasive in vivo blood glucose measurement in accordance with the present invention is illustrated. The system generally comprises a measurement unit 10 having a microwave energy source (such as a transmitter 12) operatively connected to an antenna assembly, generally comprising an antenna 14, via coaxial cable or a waveguide, generally represented as reference numeral 16. The transmitter 12 and the antenna 14 may be disposed within a common antenna housing 18, as illustrated, or disposed in separate units, provided that they are operatively connected with one another. The antenna assembly also preferably comprises a controller/processor 24, which is used to measure the amount of power/energy delivered through the antenna 14. The transmitter 12 may also be in operative communication with the controller 24.

The transmitter 12 comprises a very-low average-power microwave energy source and short duty-cycle, high-impulse power, preferably transmitting microwave frequency energy, and more preferably emitting pulsed-type microwave emissions similar to those used by radar transmitters. The transmitter 12 feeds into the antenna 14 for focusing and transmitting microwave energy towards appropriate subcutaneous blood vessels 20 located at a desired target area 50 on the patient. In use, the measurement device 10 measures the microwave energy absorbed in the near-by blood vessels 20 to aid in determining the blood glucose levels in the target area 50. More particularly, the controller 24 measures the power delivered to the blood vessels 20 by determining how much energy generated by the transmitter 12 and outputted by the antenna 14 is absorbed by the blood. As illustrated in FIG. 1, the antenna housing 18 is placed on or near the patient's skin S proximate to subcutaneous blood vessels 20 for measurement, such as on the patient's wrist.

Figure 7:
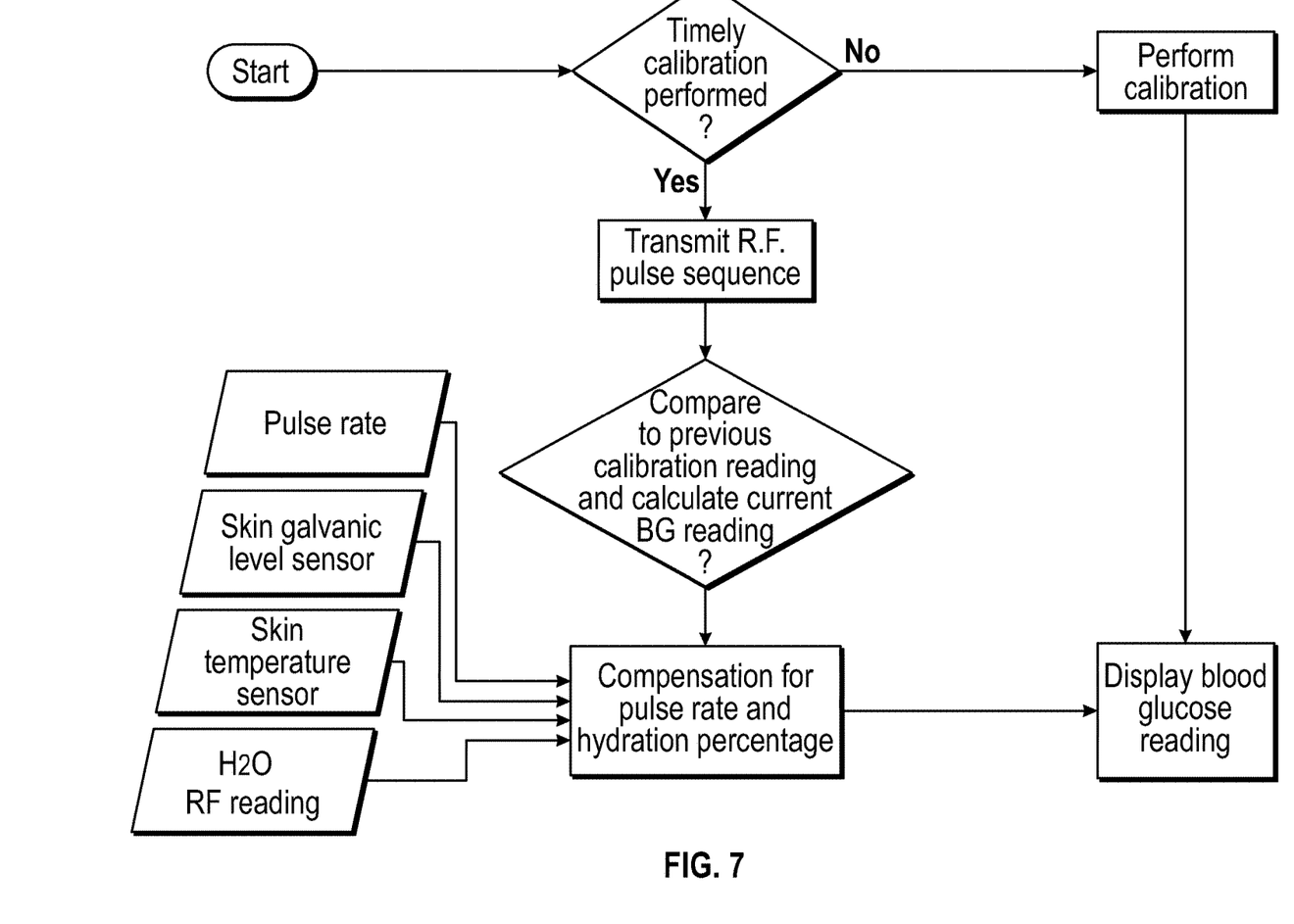
FIG. 7 provides a flow chart illustrating a test sequence in accordance with preferred embodiments of the present invention.

Referring to the schematic illustration of FIG. 7, the system achieves an accurate calculation of the patient's blood glucose levels in a defined and fixed target area 50 by measuring how much overall emitted microwave energy is transmitted to and accepted by subcutaneous, or "near surface", blood vessels 20 in the target area 50, preferably by absorption therein. Instantaneous, real-time measurement values, taken directly from the bloodstream, can be compared with a prior pre-determined calibration value. The difference, or "delta" value, between the real-time measurement value and the calibration value can provide, via analysis and calculation, a resultant current blood glucose value. In preferred embodiments, an algorithm correlating power energy values with blood glucose values is used to determine the resultant blood glucose value. Such an algorithm is preferably stored in the controller 24. The calibration value for that individual and RF mask placement can be stored in a memory buffer 22, provided as part of the controller 24.

The desired subcutaneous blood vessels 20 for accurate measurement in accordance with the present invention are typically found near the wrists of individuals, though the system of the present invention can also be used with blood vessels located in other parts of the body without departing from the spirit and principles of the present invention. Accordingly, the antenna 14 is preferably located immediately above an RF mask 52 which is placed over a desired target area, preferably by placing the antenna housing 18 over an RF mask 52 which has been placed on the skin surface S proximate to the desired target area 50. A unique and critically important part of the system of the present invention is the use of individually-tailored RF masks 52, generally illustrated in FIG. 6, for each target patient and each desired target location 50 corresponding to that individual that permits the microwave energy delivered by the antenna 14 to only reach an exact outlined target area(s) of interest, such as specific segments of near-surface blood vessels 20. By further optimizing the antenna radiation lobe pattern(s), transmitted frequencies chosen, and RF power levels used, the microwave energy is further contained, shaped, and exclusively directed to a depth in a confirming specific area that contains said "near surface" blood vessels 20. As the skin S in these areas is exceedingly thin, not only is it easy to actually physically see the blood vessel locations, but it should be also noted that these areas have almost nothing in the pathway between the antenna mask 52 and the targeted blood vessels 20 to unduly attenuate or interfere with the transmission path.

The system and method of the present invention is inherently different to other prior art systems and methods in that the present invention is a direct energy absorptive measuring system, and uniquely does not depend on measuring transmitted energy that has been transmitted from a transmitting element through layers of skin and/or other body parts to a receiving element.

Figure 6:
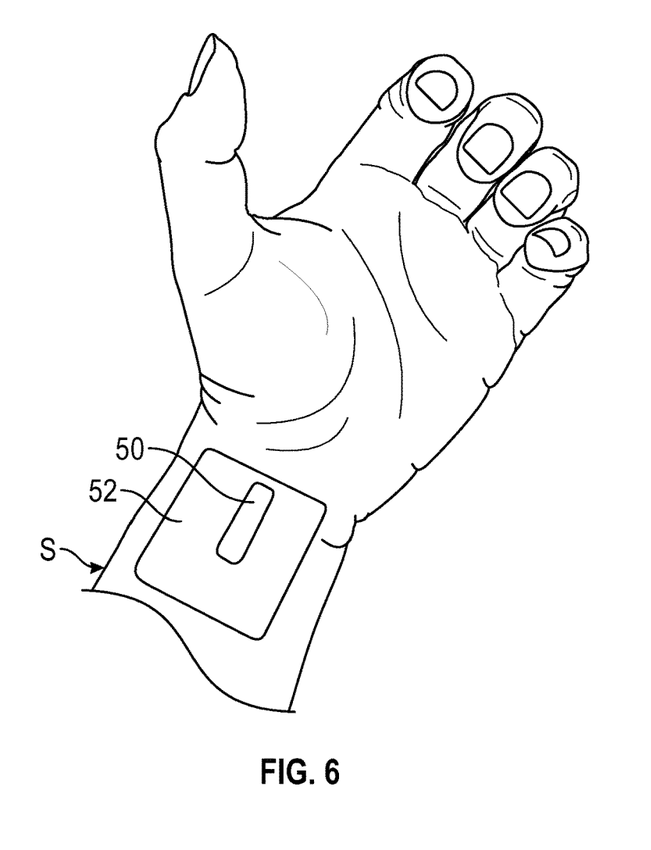

In use, an RF mask 52 is created for an individual patient, and then laid on and temporarily adhered to the patient's skin S over the desired target area 50, as generally illustrated in FIG. 6, and then used with the measurement unit 10 described herein for blood glucose measurement and tracking. The same RF mask 52 that limits the area(s) to which the RF energy is allowed to be transmitted also inherently limits the measurements of energy that otherwise would be absorbed outside of the target area 50, thus greatly increasing the accuracy of readings. Preferred methods for creating individualized RF masks 52 are described in more detail below.

In some embodiments, the RF mask 52 has a larger footprint (or surface area) than the footprint (or surface area) of the antenna assembly or antennae 14 on the surface of the desired target area 50 of the patient. The RF mask 52 having a larger footprint than the antennae assembly or antennae 14 allows for a physical X/Y axis adjustment or "slip-fit" without affecting the amount of RF energy delivered to the desired target area 50, thereby keeping the absorption amounts constant regardless of the exact location of the RF antennae 14 over the mask 52. In another embodiment of the RF mask 52, the mask may be a part of a "bracelet" type assembly that is removable and re-attachable as desired.

As noted, the power levels needed to reach the targeted subcutaneous blood vessels 20 are achieved by using pulsed-type microwave emissions, similar to, but at substantially lower power levels from those used by radar transmitters. Although the "peak" power levels may be relatively high (in order to penetrate the skin to the depth necessary), the duty cycle of these emissions is quite low, which results in the "average" power level being quite low. This makes such a wireless transmitter 12 not only very energy efficient, but also such emissions do not result in any perceptible temperature rise by the individual wearing such a system, as opposed to continuous wave emissions that are typically used in laboratory equipment.

The extrapolation process of determining the amount of energy absorbed (e.g., the power reading measurement) may utilize one or more of the following processes, either alone or in combination:

In a first approach, the antenna assembly measures one of delivered forward emitted RF peak power level and/or average power levels at a specific radio frequency over a specific time frame. More specifically, as the microwave pulses are emitted from the antenna 14, their peak transmitted power level and/or average power level are measured by the controller 24. Then, the "delta" value for the measured transmitted energy power level in comparison to a calibration value recorded at the time of the last calibration reading/measurement is determined. The system identifies, via an algorithm, a new calculated blood glucose reading that corresponds to the newly measured energy power levels. More particularly, the algorithm correlates specific blood glucose levels with energy absorption data. The calculated/determined blood glucose reading can be provided to a display and/or memory buffer, as desired.

In a second approach, instead of reading the forward power level actually delivered and/or accepted by the target blood vessels 20, the system measures the reflected energy power levels in the blood vessels 20 of the desired target area 50 to determine a "delta" value in comparison with a calibration value. In this case, lower reflected power readings would indicate a greater energy acceptance in the target area 50, which would, in turn, indicate and track with higher glucose levels. The higher the levels of glucose in the blood, the greater willingness for the blood to absorb energy, which would reduce the reflected power. As with the first approach, the calculated "delta" value, the system identifies, via the algorithm, a new calculated blood glucose reading. The calculated/determined blood glucose reading can be provided to a display and/or memory buffer, as desired.

In a third approach, the system measures Standing Wave Ratio (SWR) readings from the transmitter 12 at a specific radio frequency and from such a measurement, calculates a "delta" value in relation to calibration readings. In this case, SWR readings generally track blood glucose levels, wherein the SWR readings rise with lower levels of blood glucose, and decrease with higher levels. The calculated "delta" value is again used, via the algorithm, to determine the appropriate blood glucose reading, when can be provided to a display and/or memory buffer, as desired.

In a fourth approach, the system measures the level of input power, or current consumed, by the transmitter 12 over a specific time frame. More specifically, as the microwave pulses are emitted from the transmitter 12 while performing a diagnostic test, the input power level and/or average power level consumed by the transmitter 12 is measured by the controller 24. Then, the "delta" value for the measured input power level consumed by the transmitter 12 is compared to the input power level consumed by the transmitter 12 when last performing a calibration reading/measurement. The system identifies, via an algorithm, a new calculated blood glucose reading that corresponds to the newly measured energy power levels as compared to the last calibration power level. More particularly, the algorithm correlates specific blood glucose levels with energy absorption data. The calculated/determined blood glucose reading can be provided to a display and/or memory buffer, as desired.

The various processes listed above have all of their power measurements taking place at a fixed frequency. In accordance with a fifth approach, the transmitter 12 is commanded to sequentially vary its transmission frequency in a pre-determined fashion, frequency stepping in a repeating low-to-high, or high-to-low fashion, within a predetermined frequency range. The amount of energy acceptance from each of the individually transmitted radio frequencies utilized would be measured for either peak or average power delivered, and then compared to the other frequencies in the same measurement cycle. The shift in the absorption rate between frequencies would track changing glucose levels, and would be extrapolated to a blood glucose value using one or more extrapolation methods. One embodiment that can be used with this method would dynamically analyze the RF frequency location of whatever frequency that accepted the maximum energy absorption, which would then become the "center" or "index" frequency. This "index" frequency would be compared to the last calibration "index" frequency, to create an offset value. This offset value would be applied to a scaling algorithm to determine a calculated blood glucose value, which can then be provided to a display and/or memory buffer, as desired.

A similar approach may utilize the frequency hopping method of the fourth approach, but rather than solving for and analyzing a "center" or "index" frequency, this approach would instead analyze the energy changes in all of the various transmitted frequencies of the system to indicate the extent of "spread" or bandwidth of those frequencies that showed microwave energy absorptive activity above a predetermined threshold, and then compare the instantaneous spread of those frequencies above the threshold with the spread of the readings obtained at the last calibration. An algorithm would analyze the increase or decrease of the spread to come up with a difference value, and this value would be applied to an algorithm to calculate a blood glucose reading, which can then be provided to a display and/or memory buffer, as desired.

With each subsequent periodic microwave emission, the measurement unit 10 would record all new data, and determine a blood glucose value based on an extrapolation of the change in the delivered/accepted power level between the instantaneous power level and the previous calibration value. As an example, if the calibration entry resulted in a direct blood glucose reading of 100 and the blood at that glucose level had accepted 100 milliwatts of power from the transmitter 12 (assuming the system were using a 1:1 algorithm), a new test reading showing a 10% rise in the power delivered to the target area 50, or 110 milliwatts, would calculate to a blood glucose level of 110 mg/dl.

In addition to the base transmitter 12 and power sensing via the antenna assembly, the blood glucose tracking system and method in accordance with the present invention, can utilize additional optional compensation methods to enhance the accuracy of the blood glucose readings. Among these methods are the following:

(A) A pulse rate sensor incorporated to compensate for change in the rate of blood flow through the blood vessels 20. A faster or slower blood flow would alter the rate of energy acceptance, and could detrimentally skew the calculated results. To compensate for this, a pulse rate sensor would be optionally incorporated to allow a dynamic compensation for this variable.

(B) A skin temperature sensor in close proximity to the desired target area 50 allows for temperature compensation to be applied to optimize for changing blood vessel diameters (e.g., vasodilation; vasoconstriction) due to body core temperature variations.

(C) By measuring the skin galvanic response, this measurement, preferably along with the skin temperature monitor, can determine the level of sweat production in the area of the measurement unit 10, which could skew the microwave absorption rate. As a result, the system can compensate for sweat production based on measurement of skin galvanic data.

(D) Although blood generally averages 92% water, there are times when the hydration levels of the patient may vary widely. A periodic microwave energy measurement at a frequency more resonant for water (as opposed to one more resonant to glucose or water containing some level of glucose) could be used to continuously calibrate the measurement unit 10 to account for varying hydration levels of the patient. For example, a periodic measurement at a frequency of 22.235 GHz (the lowest resonance of a water molecule) may be taken. As the blood increases in glucose level, the resonance of the blood of the target measurement changes and becomes less resonant with the resonance of pure water (or blood which comprises a large amount of water). Either multiple microwave transmitters may be utilized, or a single wide-band transmitter which is capable of operating at a wide frequency range would allow one frequency or transmitter to be dedicated to monitoring water levels, while the other frequency or transmitter would be optimized for glucose detection, in the manner described above.

(E) It is well known that a general indication of the hydration level of an individual can be determined by physically lifting a section of skin and noting the speed in which it returns to its original 'resting' position. While this is merely a subjective test, it is based on the fact that the flexibility of the skin is directly linked to the amount of water residing in the skin. The present application offers a true objective method for directly sensing and measuring the amount of water present in the outermost layer of skin.

(F) Another known occurrence in an individual that is dehydrated is as the individual's hydration level decreases, the salt levels increase due to the lowered salt to water ratio in the blood. It is a known fact that the dialectic loss increases as the salinity increases for a given frequency and temperature. By utilizing a radio frequency optimized for water, and then measuring the dielectric loss at that frequency, a measurement that is implied by the dielectric loss may be made.

Figure 2:
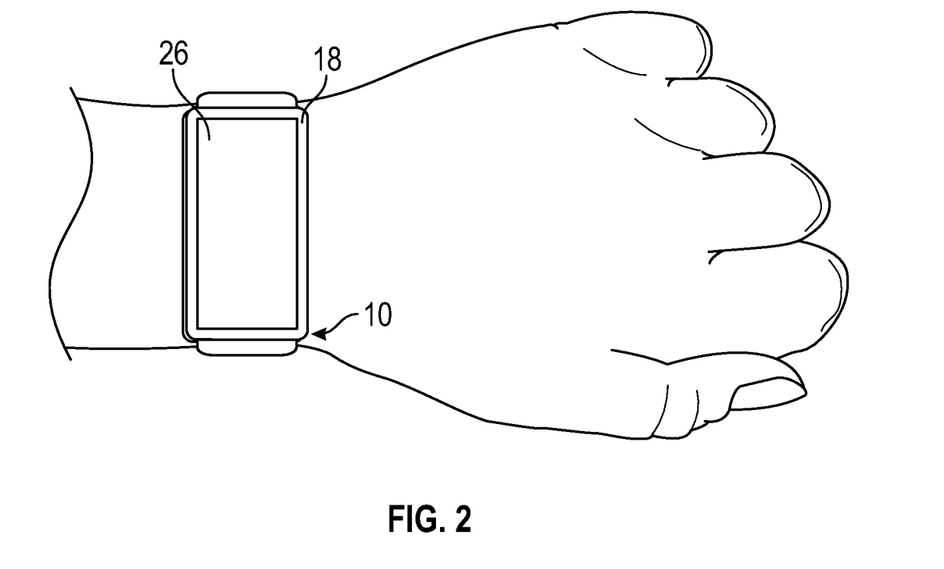
FIG. 2 illustrates another embodiment of the blood glucose tracking system in accordance with the present invention, whereby the system is embodied in a wristwatch.
Figure 3:
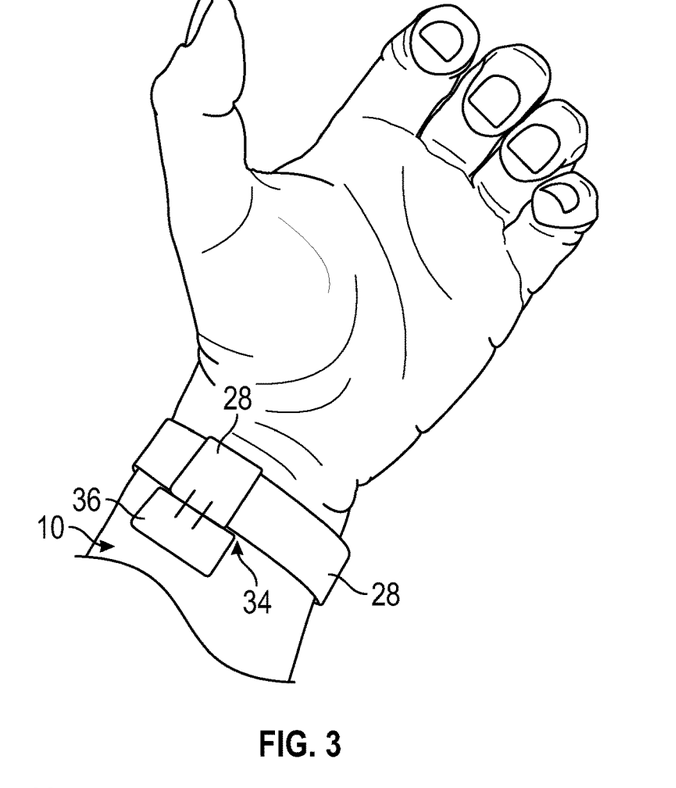
FIG. 3 illustrates yet another embodiment of the blood glucose tracking system in accordance with the present invention, whereby an auxiliary housing, including an antenna, is connected to a watch or bracelet housing a wireless transmitter, ideally worn on a wrist.
Figure 4:
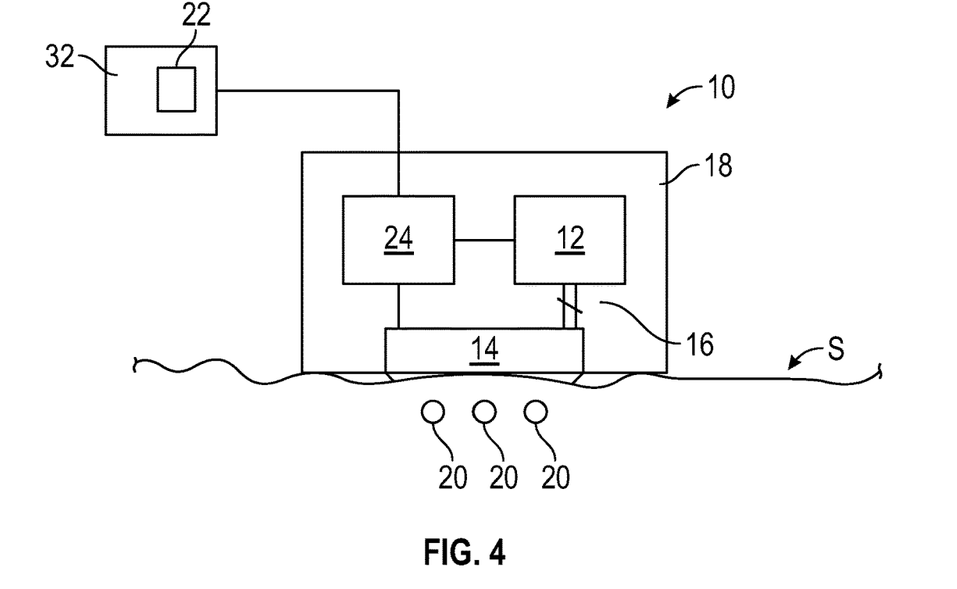
FIG. 4 illustrates a schematic embodiment of a blood glucose tracking system whereby data related to determined blood glucose levels is provided to a computer, display, or memory buffer, as desired.
Figure 5:
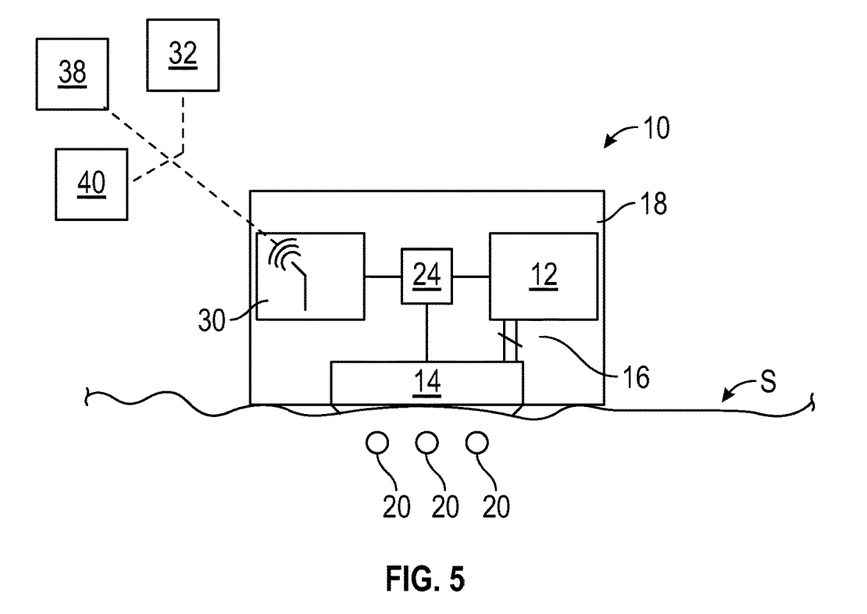
FIG. 5 illustrates another schematic embodiment of a blood glucose tracking system.

Additional measurement and display means can be provided with the measurement unit 10. For example, a display screen 26 can be provided on the antenna housing 18, as illustrated in FIGS. 2 and 4. Additionally, the measurement unit 10 can be part of or take the form of a bracelet or watch 28 worn around the wrist, or comprise a localized unit attached to the skin S, for example, by an adhesive. Additional transmitter means 30 can further be included, as schematically illustrated in FIG. 5, to transmit data from the measurement unit 10 to another unit 32, such as a computer, tablet or smart phone, for display and/or recording of blood glucose measurements taken by the measurement unit 10. For example, a measurement unit 10 in the form of a bracelet or watch 28 could store measured data, and then sync with a computer 32 for additional storage, monitoring and analysis of a patient's blood glucose measurements. The same hardware operating with modified parameters such as different frequencies and power levels may also provide for a real-time readout of hydration levels as well.

In some embodiments, the measurement unit 10 is configured to perform a blood glucose reading periodically. In some embodiments, the measurement unit 10 is configured to perform a blood glucose reading continuously (or substantially continuously), e.g. by performing one glucose reading per second. However, other sampling rates are within the scope of the present disclosure. For example, a plurality of blood glucose readings per second, such as, without limitation, three, four or five times per second, or, without limitation, one glucose reading every five seconds, every ten seconds or every thirty seconds. In some embodiments, the intervals between blood glucose readings is adjustable by the user, wearer of the measurement unit 10 and/or by a medical professional. Accordingly, an adjustable measurement unit 10 may be configured to perform a plurality of blood glucose readings per second and adjusted to perform one blood glucose reading every period of a several minutes, for example and without limitation, one blood glucose reading every five minutes. Accordingly, the blood glucose monitor or measurement unit 10 of the present disclosure is truly a continuous blood glucose monitor and may achieve greater sampling rates than conventional interstitial blood glucose measurement devices.

The blood glucose tracking system in accordance with the present invention may be a discrete "stand-alone" system, such as described above and illustrated in FIG. 1, or may be incorporated into an unrelated item worn on the wrist (such as a watch or jewelry) to take advantage of the near-surface blood vessels 20 of the wrist in a non-apparent fashion. In the instance of a watch 28, which would contain the transmitter 12 and its associated control components, a small fixed or flexible section of miniature waveguide 34 could be attached to the body of the watch 28, while the other end would connect to a detachable auxiliary "side car" antenna housing 36 placed over the desired target area for measurement. Thus, such an auxiliary antenna housing 36, including the antenna 14 and its associated control components 24, could be attached to the watch 28 for measurements, and detached when not needed. When the housings 18 and 36 are attached, the antenna 14 can be connected to the transmitter 12 via a waveguide or coaxial cable 34 running through the band of the watch 28. In the case of a watch or "smart watch" as illustrated in FIG. 2, in which a blood glucose tracking system in accordance with the present system may be incorporated as an integral part thereof, the existing digital readout 26 of the watch 28 could be used to display instantaneous blood glucose readings.

Figure 8:
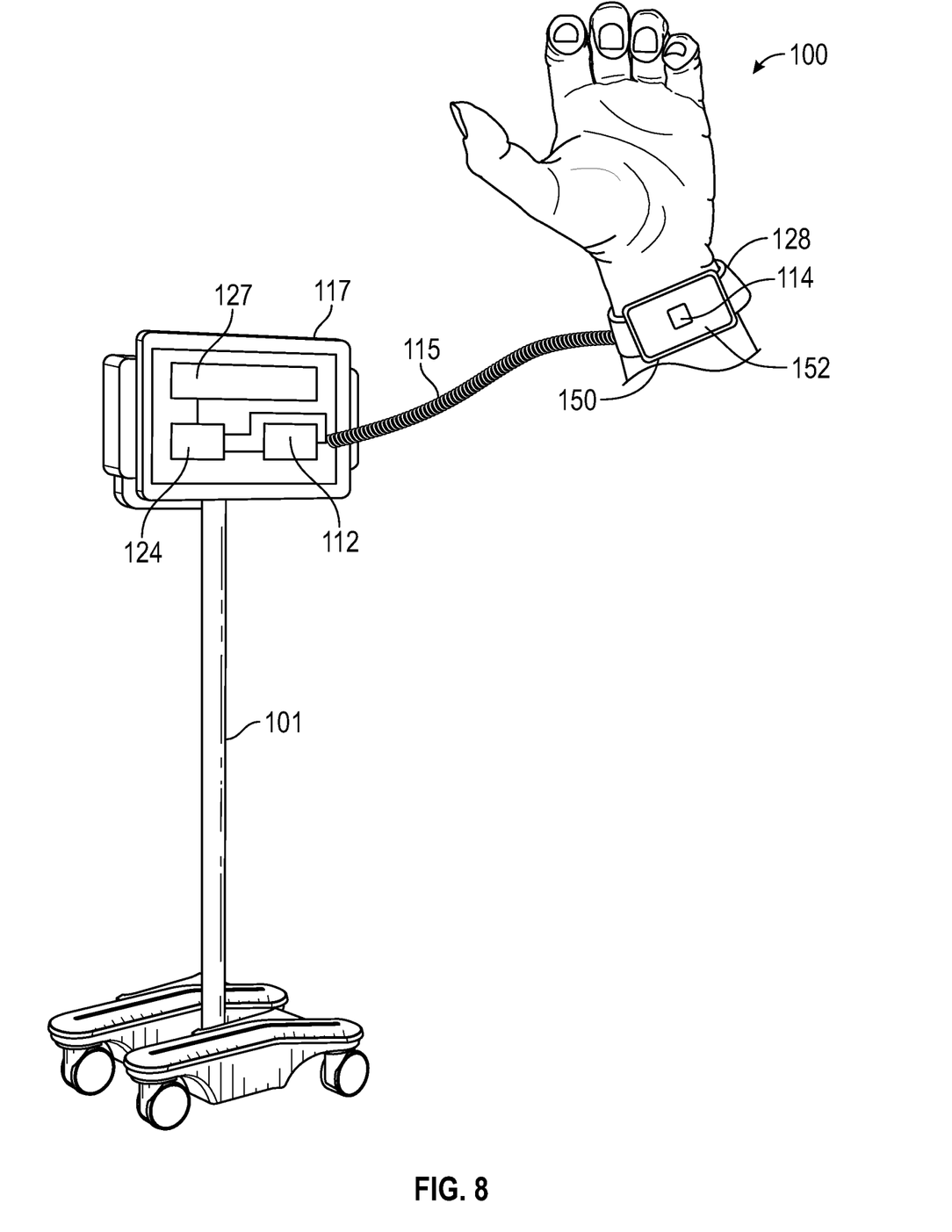
FIG. 8 illustrates another embodiment of the blood glucose tracking system in accordance with the present invention.

Referring to FIG. 8, a schematic embodiment of a continuous blood glucose monitoring system in accordance with the present disclosure is illustrated. The system is similar to the blood glucose tracking systems of FIGS. 1-6 where like reference numerals indicate like elements and function substantially the same unless otherwise indicated. The continuous blood glucose monitoring system comprises a measurement unit 100 having a microwave energy source (such as a transmitter 112) operatively connected to an antenna assembly, generally comprising an antenna 114, via a connector 115. The connector 115 comprises a coaxial cable, a waveguide, and/or other energy transmission means, and optionally data transmission means. The transmitter 112 is arranged within a housing 117. The antennae assembly and antenna 114 are arranged within the bracelet 128, which may also connected to the connector 115 or the connector 115 extends therethrough. The housing 117 of the measurement unit 100 is attached to a rolling moveable stand 101 (or to a stationary floor standing unit which is essentially the same as the rolling moveable stand 101 except having one or more legs instead of wheels) and is powered by direct connection to the mains, or by internal rechargeable batteries, e.g. with sufficient capacity to operate for one day or a plurality of consecutive days to perform a plurality of blood glucose readings without needing to be recharged in between blood glucose readings. The measurement unit 100 being attached or connected to the rolling moveable stand 101 allows for a number of continuous or non-continuous readings that may greater than number of readings a portable wearable measurement unit could provide given the power constraints or storage of portable wearable measurement unit such as a watch measurement unit.

The measurement unit 100 includes a controller/processor 124 configured to measure the amount of power/energy delivered through the antenna 114. The transmitter 112 may also be operatively connected to the controller 124. The controller 124 is arranged within the housing 117. The connector 115 connects to the housing 117 and/or extends through the housing 117 to connect to the transmitter 112. The connector 115 is flexible and is sufficient length to allow a patient to stand, sit or lay a distance away from the housing 117 (e.g. while laying in a hospital bed or on an operating table). The controller 124 is operatively connected to a display 127 on the housing 117. The controller 124 is configured to output blood glucose readings or determinations for display on the display 127.

In some embodiments, the housing 117 is configured only to provide power to the wrist-worn device, and the wrist-worn device operates substantially the same as discussed above in connection with FIGS. 1-5, and the wrist-worn device sends the data to the controller 124 and/or other components within the housing 117 wirelessly or through optional wired data transmission means contained in the connector 115 or within a different connector. In embodiments where the wrist-worn device sends the data to the housing 117, any display(s) on the wrist-worn device are optional. If the wrist-worn device includes a display, the wrist-worn device can display information corresponding to information being sent to the housing 117 about the determined blood glucose reading(s) and/or plot the blood glucose readings over time.

In some embodiments, the connector 115 is not flexible and long. For example, the connector 115 may be rigid and short in length such that the patient must be substantially near the system in order to adhere the antenna 114 against the desired target area. In some embodiments, the connector 115 and antenna assembly are integral with the housing 117, such as a cuff bracelet with antenna assembly included therein rigidly connected to the housing 117.

Numerous other creative physical embodiments may be utilized without departing from the spirit and principles of the present invention, for example, by incorporating a metal shield to limit the antenna energy towards an adjacent desired target area 50, or batteries to power the RF transmitter 12 or other equipment located within the watchband segments.

The system may also incorporate a separate data transmitter 30 (which, as noted above, is in addition to the sampling transmitter 12) to relay the raw or calculated data output to a separate display 32 or storage device 38, such as a computer, tablet or smart phone, or to a device such as an insulin pump 40. Depending on the manufacturer or model of such devices, the data output would be sent in the appropriate proprietary format for, as noted, display and/or storage.

The system and method in accordance with the present invention derive instantaneous blood glucose readings by comparing differences between a "control" reading, in which the blood glucose value is known, with an instantaneous reading, in which the blood glucose value is not known and needs to be determined. A "control" reading is a reading performed in which the blood glucose level value is known with an instantaneous reading and in which the hydration level value is not known and needs to be determined. The "control" readings can be a calibration value, which can be adjusted after each such calibration measurement using the system (e.g., a new control measurement value becomes the calibration value for the next measurement). Preferably, the hydration control readings are performed when the patient is in a non-exercise period. In order to accurately extrapolate the instantaneous glucose readings with the level of microwave energy accepted, a periodic calibration performed by an appropriate measurement method, such as by utilizing a traditional "finger stick" blood glucose testing method, or other means of accurately determining actual blood glucose levels. This data would provide the measurement unit 10 with a standard reference measurement, which would then be used to compare subsequent readings for a specific body and body target location (such as certain blood vessels in a wrist) in an individual to provide and track subsequent blood glucose readings.

In one embodiment, the determination of a subject's hydration level is determined by using different power levels and/or radio frequencies in order to sample and determine the hydration level of the skin's surface or top layer of skin. If the hydration level of a subject becomes sub-normal, the aforementioned skin area(s) will no longer contain the same amount of water for a given surface area and will therefore absorb less energy than it otherwise would. By taking a sample reading during a time of known normal hydration, any subsequent absorption level variance from the energy absorbed during the original condition would be used as the basis for an algorithm to estimate the instant hydration level.

In some embodiments, the measurement unit 10 is configured to utilize and transmit a plurality of different radio frequencies in a rapidly alternating or changing fashion so it functions in a quasi-simultaneous fashion. The different frequencies transmitted may be individually sensitive to the presence of glucose, as well as to the hydration level of an individual's blood. The measurement unit 10 is configured to output measurement data in the form of a readout (contemporaneously or non-contemporaneously) to a monitor operatively connected to the measurement unit 10. The power output readings by the RF transmitter are at their highest when matched by a load. A load may be ideally tuned to a matched antenna, an optimized "dummy load", or other kinds of loads. The readout displayed on the screen may include information regarding the overall hydration reading and/or the blood glucose reading. The measurement unit 10 is configured to record the overall hydration reading and/or the blood glucose reading over time and output a chart or other trend line to display the overall hydration reading and/or the blood glucose reading data over time on the monitor. The measurement unit 10 is configured to activate an alarm when the overall hydration reading and/or the blood glucose reading exceed one or more predetermined upper thresholds and/or one or more predetermine lower thresholds, as well as if the rate of change of any of the readings exceeds a preset time value. The upper and lower thresholds may be adjustable by a monitor operator or a medical professional.

In some embodiments, the blood glucose value and/or the hydration level value is displayed on a monitor. The measurement by the device may be performed repeatedly a plurality of times and/or continuously (or substantially continuously). The determined results from the readings may be displayed over time on the monitor forming one or more trend line(s), e.g. a blood glucose value trend line and/or a hydration level value trend line. In some embodiments, if the blood glucose value trend line is determined to decrease below a lower threshold and/or increase above an upper threshold, an alarm is activated. Similarly, if the hydration level value trend line is determined to decrease below a lower threshold and/or increase above an upper threshold, an alarm may be activated. The blood glucose value threshold(s) and/or the hydration level value threshold(s) may be adjustable by an operator.

In some embodiments, if an absolute value of the blood glucose value trend line and/or the hydration level value trend is determined to exceed a blood glucose value rate of change predetermined threshold or a hydration level value rate of change predetermined threshold, respectively, an alarm is activated. The rate of change thresholds may be adjustable by an operator.

In order to create unique individualized RF antenna masks 52, such as illustrated in FIG. 6, two preferred methods of mask creation may be utilized. The first, a "manual" method, utilizes a thin piece of Mylar or other flexible transparent material that is temporarily wrapped around an individual's wrist or other location associated with a desired target area 50, and held in place. A marking pen is used to outline the target area 50 for the antenna 14, along the width of the subject's arm or other body part, to provide subsequent positioning reference guidance. After removal, the flexible sheet is laid over a blank antenna mask material which blocks the transmission of RF energy except in those areas that are cut away and the overlay is used to guide the cutting of the mask opening area. Once the RF mask 52 is created, it can be laid on and temporarily adhered to the patient's skin S at the desired target area 50 or may be incorporated into a removable/re-attachable "bracelet" type configuration, and used with the measurement unit 10 described herein for measurement and tracking of blood glucose levels.

The second preferred RF mask creation method is an "automatic" creation method in which the desired target area 50 is photographed or scanned in the visible and/or thermal infrared spectrum. The thermal data can further be used to establish the best sensing areas. A physical measurement is also made of the general area surrounding the desired target area 50. The resulting photo data is fed into a laser cutting machine or CNC machine that scales the cutting information based upon the general area measurements, and then automatically selects and outlines the unmasked area to correspond to the optimized target area criteria. The cutting machine(s) can directly create a mask opening on a non-RF transmissive material sheet. This automatic selection process may be as a result of either the gathered visible information or the gathered IR thermal information, or both.

In accordance with embodiments according to the present disclosure, instant (or substantially instant) true blood glucose readings are provided, which are a better and more accurate reading of a person's blood glucose level than conventional interstitial fluid measuring systems and methods that rely on predictive algorithms in order to determine a future glucose level based on present interstitial readings or trends. Interstitial readings of conventional systems and methods have an inherent lag relative to the instant blood glucose readings according to the present disclosure. The predicted algorithm values of conventional systems and methods may not account for recent physiological factors such as sudden exercise, hormone release, etc., which the systems and methods of the present disclosure do not need to account for because the blood glucose readings are already resultant of these factors and are instantaneous to their actual state.

The foregoing description of embodiments of the present invention has been presented for the purpose of illustration and description. It is not intended to be exhaustive or to limit the invention to the form disclosed. Obvious modifications and variations are possible in light of the above disclosure. The embodiments described were chosen to best illustrate the principles of the invention and practical applications thereof to enable one of ordinary skill in the art to utilize the invention in various embodiments and with various modifications as suited to the particular use contemplated.

What is claimed is:

1. A method for non-invasive blood glucose measurement comprising:
    establishing a first calibration value of microwave energy at a first frequency absorption by blood located within a blood vessel that is within a pre-defined target area of a user in connection with a known blood glucose value;
    establishing a second calibration value of microwave energy at a second frequency absorption by blood located within a blood vessel that is within the pre-defined target area of the user in connection with a known hydration level value;
    transmitting microwave energy at the first frequency into blood within the blood vessel to the pre-defined target area;
    transmitting microwave energy at the second frequency into blood within the blood vessel to the pre-defined target area;
    determining a first transmitted output power of a transmitter transmitting the microwave energy at the first frequency for determining a first measurement value;
    determining a second transmitted output power of the transmitter transmitting the microwave energy at the second frequency for determining a second measurement value;
    comparing the first measurement value with the first calibration value to generate a first calculated power differential value;
    comparing the second measurement value with the second calibration value to generate a second calculated power differential value;
    determining a blood glucose value representative of the first calculated power differential value; and
    determining a hydration level representative of the second calculated power differential value.

2. The method according to claim 1, further comprising:
    displaying on a monitor the determined blood glucose value; and
    displaying on the monitor the determined hydration level value.

3. The method according to claim 1, wherein the steps are repeatedly a plurality of times, and the method further comprises:
    displaying on a monitor the determined blood glucose values over time forming a blood glucose value trend line; and
    displaying on the monitor the determined hydration level values over time forming a hydration level value trend line.

4. The method according to claim 3, further comprising:
    determining whether the blood glucose value trend line decreases below a first blood glucose value predetermined threshold or if the blood glucose value trend line increases above a second blood glucose value threshold; and
    activating an alarm if the blood glucose value trend line is determined to have decreased below the first blood glucose value predetermined threshold or if the blood glucose value trend line is determined to have increased above the second blood glucose value threshold.

5. The method according to claim 4, wherein the first blood glucose value threshold and/or the second blood glucose value threshold is configured to be adjusted by an operator.

6. The method according to claim 3, further comprising:
    determining whether an absolute value of a rate of change of the blood glucose value trend line increases above a blood glucose value rate of change predetermined threshold; and
    activating an alarm if the absolute value of the rate of change of the blood glucose value trend line has increased above the blood glucose value rate of change predetermined threshold.

7. The method according to claim 6, wherein the blood glucose value rate of change predetermined threshold is configured to be adjusted by an operator.

8. The method according to claim 3, further comprising:
    determining whether the hydration level value trend line decreases below a first hydration level value predetermined threshold or increases above a second hydration level value predetermined threshold; and activating an alarm if the hydration level value trend line is determined to have decreased below the first hydration level value predetermined threshold or if the hydration level value trend line is determined to have increased above the second hydration level value trend line predetermined threshold.

9. The method according to claim 8, wherein the first hydration level value threshold and/or the second hydration level value threshold are configured to be adjusted by an operator.

10. The method according to claim 3, further comprises:
determining whether an absolute value of a rate of change of the hydration level value trend line increases above a hydration level value rate of change predetermined threshold; and activating an alarm if the absolute value of the rate of change of the hydration level value trend line has increased above the hydration level value rate of change predetermined threshold.

11. The method according to claim 10, wherein the hydration level value rate of change predetermined threshold is configured to be adjusted by an operator.

12. The method according to claim 1, further comprising:
determining a deviation in the determined hydration level value from the hydration calibration level to proportionally correct the blood glucose value measurement.

\* \* \* \* \*